(12) United States Patent
Schwark et al.

(10) Patent No.: US 6,504,057 B2
(45) Date of Patent: Jan. 7, 2003

(54) FLUOROPHENYL-SUBSTITUTED ALKENYLCARBOXYLIC ACID GUANIDIDES, PROCESS FOR THEIR PREPARATION, THEIR USE AS A MEDICAMENT OR DIAGNOSTIC, AND MEDICAMENT CONTAINING THEM

(75) Inventors: Jan-Robert Schwark, Frankfurt (DE); Hans-Jochen Lang, Hofheim (DE); Heinz-Werner Kleemann, Bischofsheim (DE); Andreas Weichert, Egelsbach (DE); Wolfgang Scholz, Eschborn (DE); Udo Albus, Florstadt (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 10/024,388

(22) Filed: Dec. 20, 2001

(65) Prior Publication Data

US 2002/0123529 A1 Sep. 5, 2002

Related U.S. Application Data

(63) Continuation of application No. 09/778,899, filed on Feb. 8, 2001, now abandoned, which is a continuation of application No. 09/413,478, filed on Oct. 6, 1999, now abandoned, which is a continuation of application No. 09/244,177, filed on Feb. 4, 1999, now abandoned, which is a continuation of application No. 08/947,517, filed on Sep. 29, 1997, now abandoned, which is a continuation of application No. 08/651,196, filed on May 20, 1996, now abandoned.

(30) Foreign Application Priority Data

May 22, 1995 (DE) .......................................... 195 18 796

(51) Int. Cl.⁷ ..................... C07C 233/09; A61K 31/165
(52) U.S. Cl. .................. 564/182; 514/617; 514/821; 514/921; 564/161; 564/142; 564/138
(58) Field of Search ................................. 564/182, 161, 564/134, 142, 138; 514/617, 821, 921

(56) References Cited

U.S. PATENT DOCUMENTS 2,743,904 A  2/1956  Burtner
6,025,349 A  2/2000  Schwark et al.

FOREIGN PATENT DOCUMENTS

DE     44 21 536         12/1995
EP     0 688 766 B1      12/1995
WO     WO 84/00875        3/1984

OTHER PUBLICATIONS

Derwent Abstract of DE–A–44 21 536.

Primary Examiner—Shailendra Kumar
(74) Attorney, Agent, or Firm—Finnegan, Henderson, Farabow, Garrett & Dunner, LLP

(57) ABSTRACT

This invention relates to fluorophenyl-substituted alkenyl-carboxylic acid guanidides, process for their preparation, their use as a medicament or diagnostic, and medicament containing them. An embodiment of the invention embraces compounds of the formula I:

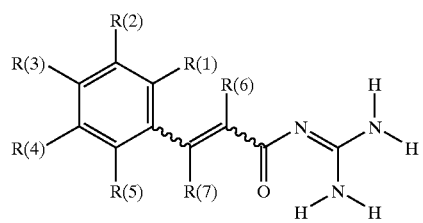

and the pharmaceutically tolerated salts thereof. The disclosed compounds are valuable inhibitors of the cellular sodium/proton exchanger ($Na^+/H^+$ exchanger). They are therefore outstandingly suitable for the treatment of all diseases attributable to increased $Na^+/H^+$ exchange.

20 Claims, No Drawings

FLUOROPHENYL-SUBSTITUTED ALKENYLCARBOXYLIC ACID GUANIDIDES, PROCESS FOR THEIR PREPARATION, THEIR USE AS A MEDICAMENT OR DIAGNOSTIC, AND MEDICAMENT CONTAINING THEM

This is a continuation of application Ser. No. 09/778,899, filed on Feb. 8, 2001, abandond which is a continuation of application Ser. No. 09/413,478, filed on Oct. 6, 1999 abandoned, which is a continuation of application Ser. No. 09/244,177, filed on Feb. 4, 1999 (abandoned), which is a continuation of application Ser. No. 08/947,517, filed on Sep. 29, 1997 (abandoned), which is a continuation of application Ser. No. 08/651,196, filed on May 20, 1996 (abandoned).

This invention relates to fluorophenyl-substituted alkenylcarboxylic acid guanidides, process for their preparation, their use as a medicament or diagnostic, and medicament containing them.

The invention further relates to alkenylcarboxylic acid guanidides carrying fluorophenyl groups, of the formula I:

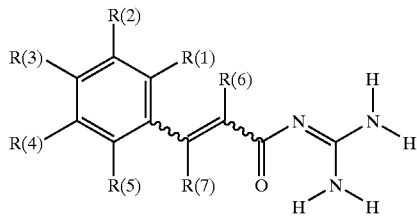

in which:
R(6) is hydrogen, $(C_1-C_9)$-alkyl, $(C_3-C_8)$-cycloalkyl or phenyl,
  the phenyl group being unsubstituted or substituted by 1–3 substituents selected from the group consisting of F, Cl, $CF_3$, methyl, methoxy and NR(9)-R(10);
R(9) and R(10) are hydrogen, $(C_1-C_4)$-alkyl or $(C_1-C_4)$-perfluoroalkyl;
R(7) is independently defined in the same way as R(6); and
R(1), R(2), R(3), R(4) and R(5) independently of one another are hydrogen or F,
  it being necessary, however, for at least one of the radicals R(1), R(2), R(3), R(4) and R(5) to be fluorine;
and their pharmaceutically tolerated salts.

Preferred compounds of the formula I are those in which:
R(6) is hydrogen, $(C_1-C_4)$-alkyl or $(C_3-C_6)$-cycloalkyl;
R(7) is independently defined in the same way as R(6); and
R(1), R(2), R(3), R(4) and R(5) independently of one another are hydrogen or F,
  it being necessary, however, for at least one of the radicals R(1), R(2), R(3), R(4) and R(5) to be fluorine;
and their pharmaceutically tolerated salts.

Particularly preferred compounds of the formula I are those in which:
R(6) is hydrogen or $CH_3$;
R(7) is hydrogen; and
R(1), R(2), R(3), R(4) and R(5) independently of one another are hydrogen or F,
  it being necessary, however, for at least one of the radicals R(1), R(2), R(3), R(4) and R(5) to be fluorine;
and their pharmaceutically tolerated salts.

If the compounds of the formula I contain one or more centers of asymmetry, these can have either the S or the R configuration. The compounds can exist as optical isomers, as diastereoisomers, as racemates or as mixtures thereof.

The double bond geometry of the compounds of the formula I can be either E or Z. The compounds can exist as a mixture of the double bond isomers.

The indicated alkyl radicals can be either linear or branched.

The invention further relates to a process for the preparation of the compound I, which comprises reacting a compound of the formula II:

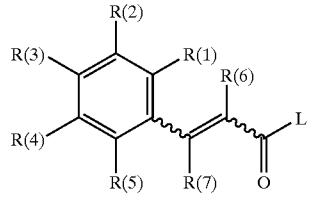

with guanidine, R(1) to R(7) being defined as indicated and L being a leaving group readily susceptible to nucleophilic substitution.

The activated acid derivatives of the formula II, in which L is an alkoxy group, preferably a methoxy group, a phenoxy group, a phenylthio, methylthio or 2-pyridyl-thio group or a nitrogen heterocycle, preferably 1-imidazolyl, are advantageously obtained in a manner known per se from the corresponding carboxylic acid chlorides (formula II, L=Cl), which can in turn be prepared in a manner known per se from the corresponding carboxylic acids (formula II, L=OH), for example with thionyl chloride.

Apart from the carboxylic acid chlorides of the formula II (L=Cl), other activated acid derivatives of the formula II can also be prepared, in a manner known per se, directly from the corresponding benzoic acid derivatives (formula II, L=OH), examples being the methyl esters of the formula II, where $L=OCH_3$, by treatment with gaseous HCl in methanol, the imidazolides of the formula II by treatment with carbonyldiimidazole [L=1-imidazolyl, Staab, Angew. Chem. Int. Ed. Engl. 1, 351–367 (1962)], the mixed anhydrides II with Cl—$COOC_2H_5$ or tosyl chloride in the presence of triethylamine in an inert solvent, and the benzoic acids activated with dicyclohexylcarbodiimide (DCC) or with O-[(cyano(ethoxycarbonyl)methylene)amino]-1,1,3,3-tetra-methyluronium tetrafluoroborate ("TOTU") [Proceedings of the 21. European Peptide Symposium, Peptides 1990, Editors E. Giralt and D. Andreu, Escom, Leiden, 1991]. A number of suitable methods for the preparation of activated carboxylic acid derivatives of the formula II are given in J. March, Advanced Organic Chemistry, Third Edition (John Wiley & Sons, 1985), p. 350, in which source literature is cited.

The reaction of an activated carboxylic acid derivative of the formula II with guanidine is carried out in a manner known per se in a protic or aprotic, polar but inert organic solvent. Solvents which have proved satisfactory in the reaction of the benzoic acid methyl esters (II, L=OMF) with guanidine are methanol, isopropanol or THF at 20° C. up to their boiling point. The majority of reactions of compounds II with salt-free guanidine have advantageously been carried out in aprotic inert solvents such as THF, dimethoxyethane or dioxane, although water can also be used as a solvent in the reaction of II with guanidine, in combination with a base such as e.g. NaOH.

If L=Cl, the reaction is advantageously carried out with the addition of an acid acceptor, e.g. in the form of excess guanidine, in order to bind the hydrohalic acid.

Some of the corresponding benzoic acid derivatives of the formula II are known and are described in the literature. The unknown compounds of the formula II can be prepared by methods known in the literature. The alkenylcarboxylic acids obtained are converted to compounds I according to the invention by one of the process variants described above.

The introduction of some substituents is effected by methods known in the literature, involving the palladium mediated cross-coupling of aryl halides or aryl triflates with e.g. organostannanes, organoboric acids, organoboranes or organocopper or organozinc compounds.

Carboxylic acid guanidides I are generally weak bases and can bind acid to form salts. Suitable acid addition salts are salts of any pharmacologically tolerated acids, for example halides, especially hydrochlorides, lactates, sulfates, citrates, tartrates, acetates, phosphates, methylsulfonates and p-toluenesulfonates.

The compounds I are substituted acylguanidines. The most prominent representative of the acylguanidines is the pyrazine derivative amiloride, which is used in therapy as a potassium-sparing diuretic. Numerous other compounds of the amiloride type are described in the literature, examples being dimethylamiloride or ethylisopropylamiloride.

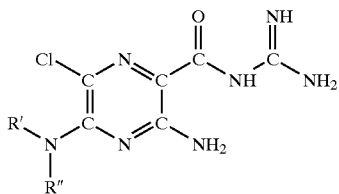

amiloride: R',R"=H
dimethylamiloride: R',R"=CH$_3$
ethylisopropylamiloride: R'=C$_2$H$_5$, R"=CH(CH$_3$)$_2$ Furthermore, studies have been disclosed which indicate that amiloride has antiarrhythmic properties (Circulation 79, 1257–63 (1989)). However, an obstacle to broad application as an antiarrhythmic is the fact that this effect is not strongly pronounced and is accompanied by a hypotensive and saluretic action, these side effects being undesirable in the treatment of cardiac dysrhythmia.

Indications of the antiarrhythmic properties of amiloride have also been obtained from experiments on isolated animal hearts (Eur. Heart J. 9 (suppl. 1): 167 (1988) (book of abstracts)). Thus, for example, it has been found on the rat heart that an artificially produced ventricular fibrillation can be completely suppressed by amiloride. The abovementioned amiloride derivative ethylisopropylamiloride was even more potent than amiloride in this model.

WO 84/00875 has disclosed cinnamic acid guanidides (R$_a$ and R$_c$ or R$_b$ and R$_d$=double bond; R(1)=substituted phenyl); in all cases, however, these are additionally substituted on the guanidine by alkyl groups, which is why they should not exhibit NHE inhibition. Moreover, halogen is only mentioned in general terms as a substituent on the phenyl ring and, although it is defined as "all four halogens", no individual example with fluorine substitution is given.

U.S. Pat. No. 2,734,904 (granted 1956) has disclosed cinnamic acid guanidides (R=substituted phenyl, alkyl= alkenylene), but only chlorine, bromine and iodine, and not fluorine, are described as halogen substituents on the phenyl ring; fluorine is excluded in the claim (halogens with an atomic number of >9 and <53).

German Offenlegungsschrift 44 21 536.3 proposes cinnamic acid guanidides (x=0, y=0), but one of the substituents R(1), R(2), R(4), R(5), R(C) or R(D) must be a perfluoroalkyl group.

It was therefore surprising that the compounds according to the invention have very good antiarrhythmic properties but no undesirable or disadvantageous salidiuretic properties. As a result of their pharmacological properties as antiarrhythmic drugs with a cardioprotective component, the compounds are outstandingly suitable for the prophylaxis and treatment of infarction and for the treatment of angina pectoris, said compounds also preventively inhibiting or greatly reducing the pathophysiological processes associated with the occurrence of ischemically induced damage, especially with the production of ischemically induced cardiac arrhythmia. By virtue of their protective actions against pathological hypoxic and ischemic situations, the compounds of the formula I according to the invention, by inhibiting the cellular Na$^+$/H$^+$ exchange mechanism, can be used as drugs for the treatment of any acute or chronic damage produced by ischemia or diseases primarily or secondarily induced by said damage. This relates to their use as drugs for operative procedures, e.g. in organ transplants, it being possible for the compounds to be used for protecting the organs in the donor before and during removal and for protecting removed organs, for example when treated with or stored in physiological baths, as well as during transfer into the recipient organism. The compounds are also valuable drugs, with a protective action, when carrying out angioplastic operative procedures, for example on the heart and on peripheral vessels. In accordance with their protective action against ischemically induced damage, the compounds are also suitable as drugs for the treatment of ischemia of the nervous system, especially the CNS, and are suitable e.g. for the treatment of stroke or cerebral edema. Furthermore, the compounds of the formula I according to the invention are also suitable for the treatment of forms of shock, for example allergic, cardiogenic, hypovolemic and bacterial shock.

Another feature of the compounds of the formula I according to the invention is their potent inhibitory action on cell proliferation, for example the proliferation of fibroblasts and the non-striated vascular myocytes. The compounds of the formula I are therefore suitable as valuable therapeutic agents for diseases where cell proliferation is a primary or secondary cause, and consequently can be used as antiatherosclerotics and agents for combating late diabetic complications, carcinosis, fibrotic diseases like pulmonary fibrosis, hepatic fibrosis or renal fibrosis, and organic hypertrophy and hyperplasia, especially hyperplasia and hypertrophy of the prostate.

The compounds according to the invention are effective inhibitors of the cellular sodium/proton exchanger (Na$^+$/H$^+$ exchanger), which, in numerous diseases (essential hypertonia, atherosclerosis, diabetes etc.), is also high in cells which are readily accessible for measurement, for example in erythrocytes, thrombocytes or leukocytes. The compounds according to the invention are therefore. suitable as outstanding and simple scientific tools, for example in their use as diagnostics for determining and distinguishing between specific forms of hypertonia, as well as atherosclerosis, diabetes, proliferative diseases etc. The compounds of the formula I are further suitable for preventive therapy to prevent the genesis of high blood pressure, for example essential hypertonia.

Drugs containing a compound I can be administered orally, parenterally, intravenously, rectally or by inhalation, the preferred administration depending on the particular characteristics of the disease. The compounds of the formula I can be administered on their own or together with galenic adjuncts, in both veterinary and human medicine.

Those skilled in the art will know, on the basis of their expert knowledge, which adjuncts are suitable for the desired drug formulation. In addition to solvents, gelling agents, suppository bases, tableting adjuncts and other excipients for active substances, it is possible to use e.g. antioxidants, dispersants, emulsifiers, anti-foams, taste correctors, preservatives, solubilizers or colorants.

For an oral form of administration, the active compounds are mixed with the appropriate additives, such as excipients, stabilizers or inert diluents, and converted by the customary methods to the appropriate forms of administration, such as tablets, coated tablets, hard gelatin capsules or aqueous, alcoholic or oily solutions. Examples of inert excipients which can be used are gum arabic, magnesia, magnesium carbonate, potassium phosphate, lactose, glucose or starch, especially cornstarch. The product can be formulated as either dry or wet granules. Examples of suitable oily excipients or solvents are vegetable or animal oils such as sunflower oil or cod-liver oil.

For subcutaneous or intravenous administration, the active compounds are brought into solution, suspension or emulsion, if desired together with the substances conventionally used for this purpose, such as solubilizers, emulsifiers or other adjuncts. Examples of suitable solvents are water, physiological saline or alcohols, e.g. ethanol, propanol or glycerol, as well as sugar solutions such as glucose or mannitol solutions, or else a mixture of the various solvents mentioned.

Examples of suitable pharmaceutical formulations or compositions for administration in the form of aerosols or sprays are solutions, suspensions or emulsions of the active substance of the formula I in a pharmaceutically acceptable solvent, such as ethanol or water in particular, or in a mixture of such solvents.

If required, the formulation can also contain other pharmaceutical adjuncts such as surfactants, emulsifiers and stabilizers, as well as a propellant gas. Such a formulation conventionally contains the active substance in a concentration of about 0.1 to 10% by weight, especially about 0.3 to 3% by weight.

The dosage of the active substance of the formula 1 to be administered, and the frequency of administration, depend on the potency and duration of action of the compounds used, on the type and severity of the disease to be treated and on the sex, age, weight and individual responsiveness of the mammal to be treated. On average the daily dose of a compound of the formula I for a patient weighing about 75 kg is at least 0.001 mg/kg, preferably 0.01 mg/kg, up to at most 10 mg/kg, preferably 1 mg/kg of body weight. In cases of acute onset of the disease, for instance immediately after suffering a cardiac infarction, even higher and particularly more frequent dosages may be necessary, e.g. up to 4 individual doses per day. Particularly in the case of i.v. administration, for instance to an infarction patient in intensive care, up to 200 mg per day may be necessary.

| List of abbreviations: | |
|---|---|
| MeOH | methanol |
| DMF | N,N-dimethylformamide |
| EI | electron impact |
| DCI | desorption - chemical ionization |
| RT | room temperature |
| EE | ethyl acetate (EtOAc) |
| mp | melting point |
| HEP | n-heptane |
| DME | dimethoxyethane |
| ES | electron spray |
| FAB | fast atom bombardment |
| $CH_2Cl_2$ | dichloromethane |
| THF | tetrahydrofuran |
| eq. | equivalent |

General Instructions for the Preparation of Alkenylcarboxylic Acid Guanidides (I)

Variant 1 A: from alkenylcarboxylic acids (II, L=OH)

1.0 eq. of the carboxylic acid derivative of the formula II is dissolved or suspended in anhydrous THF (5 ml/mmol) and then treated with 1.1 eq. of carbonyldiimidazole. After stirring for 2 hours at RT, 5.0 eq. of guanidine are introduced into the reaction solution. After stirring overnight, the THF is distilled off under reduced pressure (on a rotary evaporator), water is added, the pH is adjusted to 6 to 7 with 2 N HCl and the corresponding guanidide (formula I) is filtered off. The resulting carboxylic acid guanidides can be converted to the corresponding salts by treatment with aqueous, methanolic or ethereal hydrochloric acid or other pharmacologically tolerated acids.

Variant 1 B: from alkenylcarboxylic acid alkyl esters (II, L=O-alkyl)

1.0 eg. of the carboxylic acid alkyl ester of the formula II and 5.0 eq. of guanidine (free base) are dissolved in isopropanol or suspended in THF and refluxed (typical reaction time 2 to 5 h) until the conversion is complete (monitoring by thin layer chromatography). The solvent is distilled off under reduced pressure (Rotavapor) and the residue is taken up with EE and washed 3× with $NaHCO_3$ solution. It is dried over $Na_2SO_4$, the solvent is distilled off under vacuum and the residue is chromatographed on silica gel with a suitable eluent, e.g. EE/MeOH 5:1.

(See variant A for salt formation.)

EXAMPLE 1

E-3-(3-Fluorophenyl)acrylic acid guanidide hydrochloride

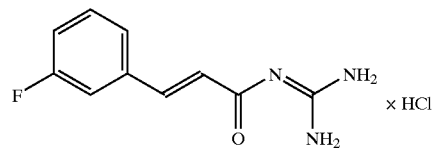

was prepared according to variant 1 A from metafluorocinnamic acid.

mp 148° C. MS: 208 (M+1)$^+$

EXAMPLE 2

E-3-(2,5-Difluorophenyl)acrylic acid guanidide hydrochloride

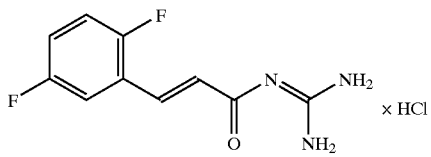

was prepared according to variant 1 A from 2,5-difluorocinnamic acid.

mp 230° C. MS: 226 (M+1)$^+$

EXAMPLE 3

E-3-(3,5-Difluorophenyl) acrylic acid guanidide hydrochloride

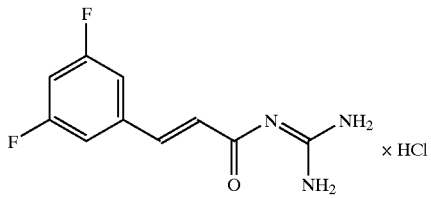

was prepared according to variant 1 A from 3,5-difluorocinnamic acid.

mp 235° C. MS: 226 (M+1)$^+$

EXAMPLE 4

E-3-(2-Fluorophenyl)acrylic acid guanidide hydrochloride

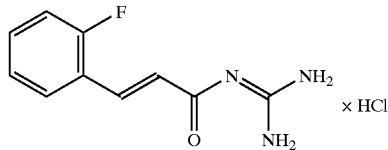

was prepared according to variant 1 A from orthofluorocinnamic acid.

mp 243° C. MS: 208 (M+1)$^+$

EXAMPLE 5

E-3-(3,5-Difluorophenyl)-2-methylacrylic acid guanidide hydrochloride

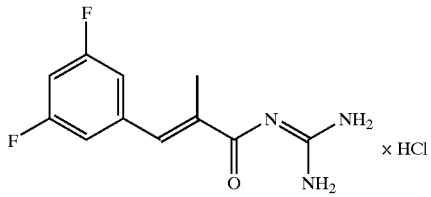

5 a) 1 eq. of triethyl 2-phosphonopropionate was deprotonated at 0° C. with 1 eq. of n-butyllithium in hexane and then treated at RT with 1 eq. of 3,5-difluorobenzaldehyde. After the aldehyde had completely reacted, the mixture was worked up with water and extracted three times by shaking with toluene. After the combined organic phases had been dried over magnesium sulfate, the solvent was removed under vacuum and the residual crude product was separated by chromatography on silica gel using EE/HEP mixtures as the eluent. Ethyl E-3-(3,5-difluorophenyl)-2-methylacrylate was isolated.

The ester from 5 a) was reacted according to variant 1 B to give E-3-(3,5-difluorophenyl)-2-methylacrylic acid guanidide and converted to the hydrochloride.

mp 178° C. MS: 240 (M+1)$^+$

EXAMPLE 6

E-3-(2-Fluorophenyl)-2-methylacrylic acid guanidide hydrochloride

E-3-(2-Fluorophenyl)-2-methylacrylic acid guanidide was synthesized from 2-fluorobenzaldehyde analogously to Example 5 and isolated as the hydrochloride.

mp 130° C. MS: 222 (M+1)$^+$

EXAMPLE 7

E-3-(4-Fluorophenyl)-2-methylacrylic acid guanidide hydrochloride

E-3-(4-Fluorophenyl)-2-methylacrylic acid guanidide was synthesized from 4-fluorobenzaldehyde analogously to Example 5 and isolated as the hydrochloride.

mp 111° C. MS: 222 (M+1)$^+$

EXAMPLE 8

E-3-(2,3,6-Trifluorophenyl)-2-methylacrylic acid guanidide hydrochloride

E-3-(2,3,6-Trifluorophenyl)-2-methylacrylic acid guanidide was synthesized from 2,3,6-trifluorobenzaldehyde analogously to Example 5 and isolated as the hydrochloride.

mp 152° C. MS: 258 (M+1)$^+$

EXAMPLE 9

E-3-(2,3,5,6-Tetrafluorophenyl)-2-methylacrylic acid guanidide hydrochloride

E-3-(2,3,5,6-Tetrafluorophenyl)-2-methylacrylic acid guanidide was synthesized from 2,3,5,6-tetrafluorobenzaldehyde analogously to Example 5 and isolated as the hydrochloride.

mp 138° C. MS: 276 (M+1)$^+$

EXAMPLE 10

E-3-(2,3,4,5,6-Pentafluorophenyl)-2-methacrylic acid guanidide hydrochloride

E-3-(2,3,4,5,6-Pentafluorophenyl)-2-methylacrylic acid guanidide was synthesized from 2,3,4,5,6-pentafluorobenzaldehyde analogously to Example 5 and isolated as the hydrochloride mp 140° C. MS: 294 (M+1)$^+$

EXAMPLE 11

E-3-(2,4,6-Trifluorophenyl)-2-methylacrylic acid guanidide hydrochloride

E-3-(2,4,6-Trifluorophenyl)-2-methylacrylic acid guanidide was synthesized from 2,4,6-trifluorobenzaldehyde analogously to Example 5 and isolated as the hydrochloride.

mp 155° C. MS: 258 (M+1)$^+$

EXAMPLE 12

E-3-(2,6-Difluorophenyl)-2-methylacrylic acid guanidide hydrochloride

E-3-(2,6-Difluorophenyl)-2-methylacrylic acid guanidide was synthesized from 2,6-difluorobenzaldehyde analogously to Example 5 and isolated as the hydrochloride mp 155° C. MS: 240 (M+1)$^+$ Inhibitors of the Na$^+$/H$^+$ exchanger of rabbit erythrocytes:

New Zealand white rabbits (Ivanovas) received a standard diet with 2% of cholesterol for six weeks in order to activate the Na$^+$/H$^+$ exchange and thus be able to determine by flame photometry the Na$^+$ influx into the erythrocytes via Na$^+$/H$^+$ exchange. The blood was taken from the auricular arteries and rendered incoagulable with 25 IU/ml of heparin potassium. Part of each sample was used for double determination of the hematocrit by centrifugation. 100 $\mu$l aliquots were used for measurement of the initial Na$^+$ content of the erythrocytes.

To determine the amiloride-sensitive sodium influx, 100 $\mu$l of each blood sample were incubated at pH 7.4 and 37° C. in 5 ml of a hyperosmolar salt/sucrose medium (mmol/1: NaCl 140, KCl 3, sucrose 150, ouabain 0.1, trishydroxymethylaminomethane 20). The erythrocytes were then washed three times with ice-cold MgCl$_2$/ouabain solution (mmol/1: MgCl$_2$ 112, ouabain 0.1) and hemolyzed in 2.0 ml of distilled water. The intracellular sodium content was determined by flame photometry.

The net Na$^+$ influx was calculated from the difference between the initial sodium values and the sodium content of the erythrocytes after incubation. The sodium influx capable of inhibition by amiloride was calculated from the difference in the sodium content of the erythrocytes after incubation with and without 3×10$^{-4}$ mol/1 of amiloride. The same procedure was also adopted for the compounds according to the invention.

Results of the inhibition of the Na$^+$/H$^+$ exchanger:

| Example | IC$_{50}$ [mol/l] |
|---|---|
| 2 | <1 |
| 3 | <1 |
| 4 | <1 |
| 5 | <1 |
| 9 | <1 |

What is claimed is:

1. A compound of the formula I:

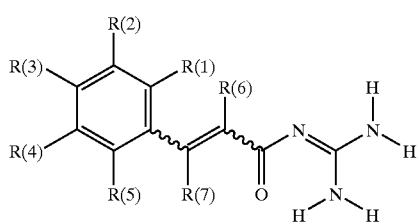

in which:

R(6) is hydrogen, (C$_1$–C$_8$)-alkyl, (C$_3$–C$_8$)-cycloalkyl or phenyl,
  the phenyl group being unsubstituted or substituted by 1–3 substituents selected from the group consisting of F, Cl, CF$_3$, methyl, methoxy and NR(9)-R(10);

R(9) and R(10) are hydrogen, (C$_1$–C$_4$)-alkyl or (C$_1$–C$_4$)-perfluoroalkyl;

R(7) is independently defined in the same way as R(6); and

R(1), R(2), R(3), R(4) and R(5) independently of one another are hydrogen or F,
  wherein at least one of the radicals R(1), R(2), R(3), R(4) and R(5) is fluorine;

or a pharmaceutically tolerated salt thereof.

2. A compound of the formula I as claimed in claim 1 wherein:

R(6) is hydrogen, (C$_1$–C$_4$)-alkyl or (C$_3$–C$_6$)-cycloalkyl;

R(7) is independently defined in the same way as R(6); and

R(1), R(2), R(3), R(4) and R(5) independently of one another are hydrogen or F,
  wherein at least one of the radicals R(1), R(2), R(3), R(4) and R(5) is fluorine.

3. A compound of the formula I as claimed in claim 1 wherein:

R(6) is hydrogen or CH$_3$;

R(7) is hydrogen; and

R(1), R(2), R(3), R(4) and R(5) independently of one another are hydrogen or F,
  wherein at least one of the radicals R(1), R(2), R(3), R(4) and R(5) is fluorine.

4. A process for the preparation of a compound of the formula I as claimed in claim 1, which comprises reacting a compound of the formula II:

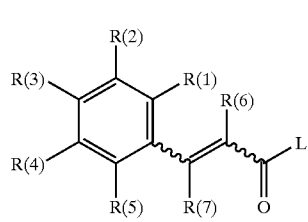

with guanidine, wherein R(1) to R(7) are defined as in claim 1 and L is a leaving group readily susceptible to nucleophilic substitution.

5. A process as claimed in claim 4 wherein the leaving group L is selected from the group consisting of alkoxy, phenoxy, phenylthio, methylthio, 2-pyridyl-thio, and a nitrogen heterocycle.

6. A method of treating arrhythmia comprising administering to a host in need of said treatment an effective amount of a compound of the formula I as claimed in claim 1.

7. A method of treating arrhythmia, which comprises combining an effective amount of a compound I as claimed in claim 1 with a conventional additive to form a composition and administering the composition in a form suitable for administration.

8. A method of treating cardiac infarction comprising administering to a host in need of said treatment an effective amount of a compound of the formula I as claimed in claim 1.

9. A method of treating angina pectoris comprising administering to a host in need of said treatment an effective amount of a compound of the formula I as claimed in claim 1.

10. A method of treating ischemic heart conditions comprising administering to a host in need of said treatment an effective amount of a compound of the formula I as claimed in claim 1.

11. A method of treating ischemic conditions of the peripheral and central nervous system and stroke comprising administering to a host in need of said treatment an effective amount of a compound of the formula I as claimed in claim 1.

12. A method of treating ischemic conditions of peripheral organs and extremities comprising administering to a host in need of said treatment an effective amount of a compound of the formula I as claimed in claim 1.

13. A method of treating shock conditions comprising administering to a host in need of said treatment an effective amount of a compound of the formula I as claimed in claim 1.

14. A method of protecting organs during surgical operations and organ transplants comprising administering an effective amount of a compound of the formula I as claimed in claim 1.

15. A method of preserving or storing transplants for surgical procedures comprising administering an effective amount of a compound of the formula I as claimed in claim 1.

16. A method of treating diseases where cell proliferation is a primary or secondary cause comprising administering to a host in need of said treatment an effective amount of a compound of the formula I as claimed in claim 1.

17. A method for combating late diabetic complications, carcinosis, fibrotic diseases, and hyperplasia of the prostate comprising administering to a host in need of said treatment administering an effective amount of a compound of the formula I as claimed in claim 1.

18. A method of inhibiting the $Na^+/H^+$ exchanger for the diagnosis of hypertonia and proliferative diseases comprising administering an effective amount of a compound of the formula I as claimed in claim 1 as a diagnostic agent.

19. A pharmaceutical composition comprising an effective amount of a compound of the formula I as claimed in claim 1.

20. A method of treating an ischemic heart condition, an ischemic condition of the peripheral or central nervous system, or an ischemic condition of a peripheral organ or extremity, comprising administering to a host in need of said treatment an effective amount of a compound of the formula I as claimed in claim 1.

* * * * *